United States Patent [19]

Haag et al.

[11] 4,097,543

[45] Jun. 27, 1978

[54] SELECTIVE DISPROPORTIONATION OF TOLUENE

[75] Inventors: Werner O. Haag, Lawrenceville; David H. Olson, Pennington, both of N.J.

[73] Assignee: Mobil Oil Corporation, New York, N.Y.

[21] Appl. No.: 760,893

[22] Filed: Jan. 21, 1977

Related U.S. Application Data

[63] Continuation-in-part of Ser. No. 685,869, May 12, 1976, abandoned, and a continuation-in-part of Ser. No. 685,872, May 12, 1976, abandoned.

[51] Int. Cl.$^2$ ................................................ C07C 3/62
[52] U.S. Cl. ................................................ 260/672 T
[58] Field of Search ................................... 260/672 T

[56] References Cited

U.S. PATENT DOCUMENTS

| | | | |
|---|---|---|---|
| 3,926,872 | 12/1975 | Plank et al. | 260/672 T |
| 3,957,621 | 5/1976 | Bonacci et al. | 260/672 T |

*Primary Examiner*—C. Davis

*Attorney, Agent, or Firm*—Charles A. Huggett; Raymond W. Barclay

[57] ABSTRACT

A catalytic process is provided for the selective production of para-xylene by disproportionation of toluene in the presence of a catalyst comprising a crystalline aluminosilicate zeolite having a silica to alumina ratio of at least about 12 and a constraint index within the approximate range of 1 to 12, which catalyst has undergone controlled precoking, i.e. selectivation, by exposing the same to a thermally decomposable organic compound at a temperature in excess of the decomposition temperature of said compound, generally greater than 1000° F., but less than about 1200° F., at a hydrogen to organic compound mole ratio between 0 and 1 to deposit at least about 2 weight percent coke thereon and thereafter contacting toluene with the resulting coke-containing catalyst under disproportionation conditions including a temperature between about 800° F. and 1025° F., and preferably between about 825° F. and 1000° F., at a hydrogen to toluene mole ratio greater than 1 and up to about 10 and recovering a product mixture containing para-xylene in an amount greater than the thermodynamic equilibrium concentration thereof in the total xylenes produced.

19 Claims, 2 Drawing Figures

SELECTIVE DISPROPORTIONATION OF TOLUENE

CROSS REFERENCE TO RELATED APPLICATIONS

This application is a continuation-in-part of application Ser. No. 685,869 and application Ser. No. 685,872, both of which were filed May 12, 1976, and both of which are now abandoned.

BACKGROUND OF THE INVENTION

1. Field of the Invention

This invention relates to a process for selective disproportionation of toluene to yield para-xylene, utilizing a specified crystalline aluminosilicate zeolite catalyst which has undergone prior treatment to deposit a controlled amount of coke thereon.

2. Description of the Prior Art

The disproportionation of aromatic hydrocarbons in the presence of zeolite catalysts has been described by Grandio et al. in the Oil and Gas Journal, Vol. 69, No. 48 (1971). U.S. Pat. Nos. 3,126,422; 3,413,374; 3,598,878; 3,598,879 and 3,607,961 show vapor-phase disproportionation of toluene over various catalysts.

In these prior art processes, the xylene product produced has the equilibrium composition of approximately 24 percent para, 54 percent meta and 22 percent ortho.

While the above-noted prior art is considered of interest in connection with the subject matter of the present invention, the conversion process described herein, utilizing a catalyst which has undergone controlled precoking comprising a crystalline aluminosilicate zeolite characterized by a silica to alumina ratio of at least about 12 and a constraint index within the approximate range of 1 to 12, has not, insofar as is known, been heretofore described.

Of the xylene isomers, i.e. ortho, meta and paraxylene, meta-xylene is the least desired product, with ortho and para-xylene being the more desired products. Para-xylene is of particular value being useful in the manufacture of terephthalic acid which is an intermediate in the manufacture of synthetic fibers, such as "Dacron". Mixture of xylene isomers, either alone or in further admixture with ethylbenzene, generally containing a concentration of about 24 weight percent para-xylene in the equilibrium mixture, have previously been separated by expensive superfractionation and multistage refrigeration steps. Such process, as will be realized, has involved high operation costs and has a limited yield.

SUMMARY OF THE INVENTION

In accordance with the present invention, there has been discovered a process for the selective production of paraxylene by disproportionation of toluene, in the presence of a crystalline aluminosilicate catalyst which has undergone precoking by contact with a thermally decomposable organic compound at an elevated temperature to deposit at least about 2 weight percent of coke thereon and thereafter contacting toluene under disproportionation conditions with the coke-containing catalyst to yield a product in which para-xylene is present in an amount greater than the thermodynamic equilibrium concentration thereof in the total xylenes produced. The crystalline aluminosilicate zeolite is essentially characterized by a silica to alumina ratio of at least about 12 and a constraint index, as hereinafter defined, within the approximate range of 1 to 12. The coke selectivated catalyst is further desirably characterized by a xylene sorption capacity greater than 1 gram/100 grams of zeolite and an ortho xylene sorption time for 30 percent of said capacity of greater than 100 minutes, the sorption capacity and sorption time being measured at 120° C. and a xylene pressure of 4.5±0.8 mm of mercury.

In a preferred embodiment, the present process comprises conversion of toluene to yield xylenes in which the proportion of para-xylene is substantially in excess of its normal equilibrium concentration and preferably in excess of 40 weight percent of the xylene product produced in the presence of the specified precoked catalyst at a temperature between about 800 and 1025° F. at a pressure between about 1 and about 100 atmospheres and a hydrogen to toluene mole ratio greater than 1 and up to about 10, utilizing a feed weight hourly space velocity (WHSV) between about 0.5 and about 50. The latter WHSV is based upon the weight of catalyst composition, i.e. total weight of active catalyst and binder therefor. The effluent is separated and distilled to remove the desired product, e.g. para-xylene and unreacted material may be recycled for further reaction.

In a particular embodiment of the invention, toluene is employed as the source of coke for deposition on the surface of the zeolite catalyst. In such instance, toluene is brought into initial contact with the catalyst at a temperature greater than 1000° F. up to about 1200° F. at a hydrogen/toluene mole ratio between 0 and about 1. Thereafter, the toluene feed is disproportionated in the presence of the coke-containing catalyst under the conditions indicated hereinabove.

DESCRIPTION OF SPECIFIC EMBODIMENTS

Figure 1:
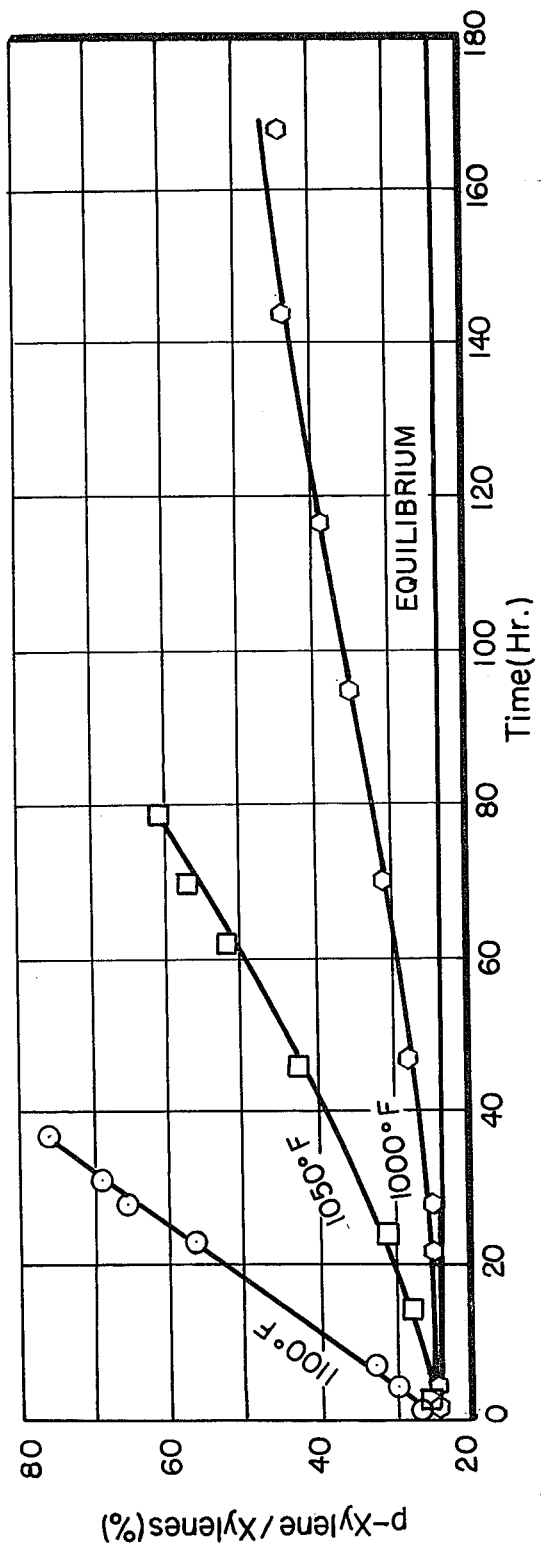
FIG. 1 shows the relationship between the rate of para-xylene selectivity increase and temperature of precoking of the catalyst.

The process of this invention is concerned with disproportionation of toluene to yield benzene and xylenes in which the para-xylene isomer is selectively produced. Such result is achieved by conducting the disproportionation reaction in the presence of a crystalline aluminosilicate catalyst which has undergone precoking to deposit at least about 2 weight percent of coke thereon as a result of being exposed to a thermally decomposable organic compound at a temperature in excess of the decomposition temperature of said compound but less than about 1200° F. at a hydrogen to organic compound mole ratio between 0 and 1. For toluene and organic compounds of similar reactivity, the temperature employed is greater than 1000° F. With organic compounds that are more readily decomposable than toluene, such as, for example, phenols and styrene, precoking can be carried at temperatures less than 1000° F. With the use of higher temperatures in the aforenoted range, the presence of hydrogen has not been found necessary. With temperatures of less than about 1100° F., preferably some hydrogen, generally at least 0.2 mole of hydrogen per mole of organic compound is desirable to yield a more stable catalyst. Contact between toluene feed and the precoked catalyst is then established under disproportionation conditions including a temperature between about 800° F. and 1025° F. and preferably between about 825° F. and 1000° F. at a hydrogen to toluene mole ratio greater than 1 and up to about 10 and preferably between about 1.2 and about 10 at a pressure between about 1 atmosphere and about 100 atmospheres utilizing a weight hourly space velocity of between about 0.5 and about 50.

In accordance with the present invention, toluene is brought into contact, under disproportionation conditions, with a bed comprising particle-form catalyst containing a crystalline aluminosilicate zeolite having a silica to alumina ratio of at least about 12 and a constraint index within the approximate range of 1 to 12. The catalyst, prior to contacting with toluene under disproportionation conditions, has deposited thereon a controlled amount of coke as a result of exposure to a thermally decomposable organic compound at an elevated temperature below the temperature at which crystallinity of the zeolite is adversely affected. Generally, this temperature will be less than about 1200° F.

Organic materials, thermally decomposable under the above temperature conditions to provide coke deposition, encompass a wide variety of compounds including by way of example, hydrocarbons, such as paraffinic, cycloparaffinic, olefinic, cycloolefinic and aromatic; oxygen-containing organic compounds such as alcohols, aldehydes, ethers, ketones and phenols; heterocyclics such as furans, thiophenes, pyrroles and pyridines. Usually, it is contemplated that a thermally decomposable hydrocarbon, such as an alkyl-substituted aromatic, will be the source of coke and most preferably toluene itself. In the latter case, toluene is initially brought into contact under conditions of temperature and hydrogen concentration amenable to rapid coke formation and when the desired coke deposition has been effected, toluene feed is continued in contact with the coke-containing catalyst under conditions of temperature and hydrogen concentration conducive to disproportionation, with a greatly reduced coking rate.

The amount of coke deposited on the catalyst, prior to contact with toluene under disproportionation conditions, will ordinarily be at least about 2 weight percent. Generally, the amount of coke deposited will not exceed about 60 weight percent. The optimum amount of coke to be employed in a given toluene disproportionation process in accordance with the present invention will depend on the conditions at which the desired disproportionation is effected including among other variables, the crystal size of the aluminosilicate zeolite used and the nature of the catalyst binder, if any, employed.

While it is contemplated that the process described herein may involve use of a crystalline aluminosilicate zeolite of any crystal size, it is preferred that the zeolite crystal size be greater than about 0.5 micron, more preferably in the approximate range of 1 to 20 microns and particularly 1 to 6 microns. It has been found that as a general rule, the smaller the zeolite crystal size, the greater the amount of coke deposition required to achieve comparable results. Thus, on a binder-free basis, it has been observed that with the use of small zeolite crystals, e.g. in the range of 0.02 to 0.05 micron size, greater than 20 weight percent of coke deposition was required to obtain results comparable to those obtained with larger zeolite crystals, e.g. in the range of 1 to 2 microns, having approximately 4 weight percent of coke deposited thereon.

In assessment of zeolite crystal size, conventional scanning electron microscopy (SEM) techniques can be used, the minimum crystal dimension of a given crystal being taken as the dimension of reference. The crystalline aluminosilicate zeolites preferably used in the present invention in substantial proportion are essentially characterized by a crystal size of greater than about 0.5 micron. It is contemplated that the amount of zeolite of such crystal size will be such as to exert a directive influence in the desired selective production of para-xylene. Generally, the amount of zeolite of such crystal size will be present in predominate proportion, i.e. in an amount exceeding 50 weight percent, and preferably may constitute up to 100 weight percent of the total zeolite employed.

The amount and nature of the binder composited with the crystalline aluminosilicate zeolite also has been found to have a marked effect on the amount of coke deposition required to obtain the desired selective production of para-xylene. Thus, while binder-free zeolite of 1 to 2 micron size afforded high para-xylene selectivity with about 4 weight percent of coke deposited thereon, comparable use of a composite of such zeolite (65 percent) and alumina (35 percent) required an average of about 22 weight percent of coke deposition. With the use of small zeolite crystals (0.02 to 0.05 micron) and alumina binder (35 percent), it is contemplated that 40 percent or more coke deposition would be required to obtain the desired high para-xylene selectivity. Also, increase in alumina content of the zeolite composite, which desirably is in the form of an extrudate, would be expected to require increased coke deposition to obtain comparable high para-xylene selectivity. With the use of other binders, such as clay or silica, it is anticipated that the amount of coke required for comparable results may be somewhat less than in the case where alumina is the sole binding material.

The precoked crystal aluminosilicate zeolites employed in the process described herein are further desirably characterized by certain hydrocarbon sorption capacities and rates. Measurements of such properties are conveniently carried out gravimetrically in a thermal balance. In particular, it has been found that an equilibrium sorption capacity of xylene, which can be either para, meta, ortho or a mixture thereof, preferably para-xylene since this isomer reaches equilibrium within the shortest time of at least 1 gram per 100 grams of zeolite measured at 120° C. and a xylene pressure of 4.5±0.8 mm of mercury and an ortho-xylene sorption time for 30 percent of said capacity of greater than 100 minutes (at the same conditions of temperature and pressure) are required in order to achieve the desired selective production of para-xylene.

It has been found that zeolites exhibiting very high selectivity for para-xylene production require a very long time up to and exceeding a thousand minutes to sorb o-xylene in an amount of 30% of total xylene sorption capacity. For those materials it is more convenient to determine the sorption time for a lower extent of sorption, such as 5%, 10% or 20% of capacity, and to estimate the 30% sorption time by applying the following multiplication factors F as illustrated for 5% sorption:

| $t_{0.3} = F \cdot t_{0.05}$ Percent of sorption capacity | Factor(F) to Estimate 30% Sorption Time |
|---|---|
| 5 | 36 |
| 10 | 9 |
| 20 | 2.2 |

Particularly preferred are those zeolites having a silica to alumina ratio of at least about 12 and a constraint index within the approximate range of 1 to 12. These zeolites induce profound transformations of aliphatic hydrocarbons to aromatic hydrocarbons in commercially desirable yields and are generally highly effective in conversion reactions involving aromatic hydrocarbons. Although they have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These zeolites retain their crystallinity for long periods in spite of the presence of steam at high temperature which induces irreversible collapse of the framework of other zeolites, e.g. of the X and A type.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolites is not of the desired type. Windows of 10-membered rings are preferred, although, in some instances, excessive puckering or pore blockage may render these zeolites ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} (\text{fraction of n-hexane remaining})}{\log_{10} (\text{fraction of 3-methylpentane remaining})}$$

The constraint index approximates the ratio of the cracking rate constants for the two hydrocarbons. Zeolites suitable for the present invention are those having a constraint index in the approximate range of 1 to 12. Constraint Index (CI) values for some typical zeolites are:

| CAS | C.I. |
|---|---|
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 0.6 |
| ZSM-4 | 0.5 |
| H-Zeolon | 0.4 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possibly occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with the probability, in some instances, of compounding variable extremes. However, in all instances, at a temperature within the above-specified range of 550° F. to 950° F., the constraint index will have a value for any given zeolite of interest herein within the approximate range of 1 to 12.

The class of zeolites defined herein is exemplified by ZSM-5, ZSM-11, ZSM-12, ZSM-35, ZSM-38, and other similar materials. U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-38 is more particularly described in U.S. Application Ser. No. 528,060, filed Nov. 29, 1974 and now abandoned. This zeolite can be identified, in terms of mole ratios of oxides and in the anhydrous state, as follows:

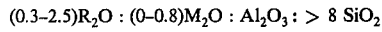
$(0.3-2.5)R_2O : (0-0.8)M_2O : Al_2O_3 : > 8 SiO_2$ wherein R is an organic nitrogen-containing cation derived from a 2-(hydroxyalkyl) trialkylammonium compound and M is an alkali metal cation, and is characterized by a specified X-ray powder diffraction pattern.

In a preferred synthesized form, the zeolite has a formula, in terms of mole ratios of oxides and in the anhydrous state, as follows:

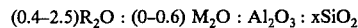
$(0.4-2.5)R_2O : (0-0.6) M_2O : Al_2O_3 : xSiO_2$ wherein R is an organic nitrogen-containing cation derived from a 2-(hydroxyalkyl) trialkylammonium compound, wherein alkyl is methyl, ethyl or a combination thereof, M is an alkali metal, especially sodium, and x is from greater than 8 to about 50.

The synthetic ZSM-38 zeolite possesses a definite distinguishing crystalline structure whose X-ray diffraction pattern shows substantially the significant lines set forth in Table I. It is observed that this X-ray diffraction pattern (significant lines) is similar to that of natural ferrierite with a notable exception being that natural ferrierite patterns exhibit a significant line at 11.33A.

TABLE I

| d (A) | I/I$_o$ |
|---|---|
| 9.8 ± 0.20 | Strong |
| 9.1 ± 0.19 | Medium |
| 8.0 ± 0.16 | Weak |
| 7.1 ± 0.14 | Medium |
| 6.7 ± 0.14 | Medium |
| 6.0 ± 0.12 | Weak |
| 4.37 ± 0.09 | Weak |
| 4.23 ± 0.09 | Weak |
| 4.01 ± 0.08 | Very Strong |
| 3.81 ± 0.08 | Very Strong |
| 3.69 ± 0.07 | Medium |
| 3.57 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |
| 2.92 ± 0.06 | Medium |
| 2.73 ± 0.06 | Weak |
| 2.66 ± 0.05 | Weak |
| 2.60 ± 0.05 | Weak |

TABLE I-continued

| d (A) | I/I$_o$ |
|---|---|
| 2.49 ± 0.05 | Weak |

A further characteristic of ZSM-38 is its sorptive capacity providing said zeolite to have increased capacity for 2-methylpentane (with respect to n-hexane sorption by the ratio n-hexane/2-methyl-pentane) when compared with a hydrogen form of natural ferrierite resulting from calcination of an ammonium exchanged form. The characteristic sorption ratio n-hexane/2-methylpentane for ZSM-38 (after calcination at 600° C.) is less than 10, whereas that ratio for the natural ferrierite is substantially greater than 10, for example, as high as 34 or higher.

Zeolite ZSM-38 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| | Broad | Preferred |
|---|---|---|
| R+ | | |
| R+ + M+ | 0.2–1.0 | 0.3–0.9 |
| OH$^-$/SiO$_2$ | 0.05–0.5 | 0.07–0.49 |
| H$_2$O/OH$^-$ | 41–500 | 100–250 |
| SiO$_2$/Al$_2$O$_3$ | 8.8–200 | 12–60 | wherein R is an organic nitrogen-containing cation derived from a 2-(hydroxyalkyl) trialkylammonium compound and M is an alkali metal ion, and maintaining the mixture until crystals of the zeolite are formed. (The quantity of OH$^-$ is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time of from about 6 hours to about 100 days. A more preferred temperature range is from about 150° C. to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is thereafter dried, e.g. at 230° F. for from about 8 to 24 hours.

ZSM-35 is more particularly described in U.S. Application Ser. No. 528,061, filed Nov. 29, 1974. This zeolite can be identified, in terms of mole ratios of oxides and in the anhydrous state, as follows:

$(0.3-2.5)R_2O : (0-0.8)M_2O : Al_2O_3 : > 8 SiO_2$ wherein R is an organic nitrogen-containing cation derived from ethylenediamine or pyrrolidine and M is an alkali metal cation, and is characterized by a specified X-ray powder diffraction pattern.

In a preferred synthesized form the zeolite has a formula, in terms of mole ratios of oxides and in the anhydrous state, as follows:

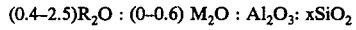
$(0.4-2.5)R_2O : (0-0.6) M_2O : Al_2O_3 : xSiO_2$ wherein R is an organic nitrogen-containing cation derived from ethylenediamine or pyrrolidine, M is an alkali metal, especially sodium, and x is from greater than 8 to about 50.

The synthetic ZSM-35 zeolite possesses a definite distinguishing crystalline structure whose X-ray diffraction pattern shows substantially the significant lines set forth in Table II. It is observed that this X-ray diffraction pattern (with respect to significant lines) is similar to that of natural ferrierite with a notable exception being that natural ferrierite patterns exhibit a significant line at 11.33A. Close examination of some individual samples of ZSM-35 may show a very weak line at 11.3-11.5A. This very weak line, however, is determined not to be a significant line for ZSM-35.

TABLE II

| d (A) | I/I$_o$ |
|---|---|
| 9.6 ± 0.20 | Very Strong - Very Very Strong |
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak Medium |
| 3.14 ± 0.06 | Weak Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

A further characteristic of ZSM-35 is its sorptive capacity proving said zeolite to have increased capacity for 2-methylpentane (with respect to n-hexane sorption by the ratio n-hexane/2-methylpentane) when compared with a hydrogen form of natural ferrierite resulting from calcination of an ammonium exchanged form. The characteristic sorption ratio n-hexane/2-methylpentane for ZSM-35 (after calcination at 600° C.) is less than 10, whereas that ratio for the natural ferrierite is substantially greater than 10, for example, as high as 34 or higher.

Zeolite ZSM-35 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH$^-$/SiO$_2$ | 0.05–0.5 | 0.07–0.49 |
| H$_2$O/OH$^-$ | 41–500 | 100–250 |
| SiO$_2$/Al$_2$O$_3$ | 8.8–200 | 12–60 | wherein R is an organic nitrogen-containing cation derived from pyrrolidine or ethylenediamine and M is an alkali metal ion, and maintaining the mixture until crystals of the zeolite are formed. (The quantity of OH− is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time of from about 6 hours to about 100 days. A more preferred temperature range is from about 150° C. to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is dried, e.g. at 230° F., for from about 8 to 24 hours.

The specific zeolites described, when prepared in the presence of organic cations, are catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-38 and ZSM-35, with ZSM-5 particularly preferred.

In a preferred aspect of this invention, the zeolites hereof are selected as those having a crystal framework density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred zeolites of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

In practicing the desired disproportionation process, it may be desirable to incorporate the above described crystalline aluminosilicate zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix may vary widely with the zeolite content ranging from between about 1 to about 99 percent by weight and more usually in the range of about 5 to about 80 percent by weight of the composite.

The disproportionation process described herein may be carried out as a batch type, semi-continuous or continuous operation utilizing a fixed or moving bed catalyst system. The catalyst after use is regenerated whereby coke is burned to a desired extent from the catalyst in an oxygen-containing atmosphere, e.g. air, at an elevated temperature, elevated pressure is also desirable.

The following examples will serve to illustrate the process of the invention without limiting the same:

EXAMPLE 1

42.2 pounds of Q-Brand sodium silicate were mixed with 52.8 pounds of water. The resulting solution is designated Solution A. 1.35 pounds of commercial grade aluminum sulfate $(Al_2(SO_4)_3 \cdot 14H_2O)$, 15.84 pounds of commercial grade NaCl, and 3.52 pounds of $H_2SO_4$ (96.5 wt. % $H_2SO_4$) were mixed with 72.2 pounds of water. The resulting solution is designated Solution B. 2.6 pounds of water were added to an autoclave equipped with high shear agitation. Solution A and Solution B were mixed simultaneously in a nozzle and sprayed into the autoclave. The resulting gel was mixed in the autoclave at 90 RPM and ambient temperature for 1 hour. 2.84 pounds of tri-n-propylamine and 2.44 pounds of n-propyl bromide were added to the contents of the autoclave. The mixture was reacted at 320° F. with 90 RPM agitation. After 20 hours at 320° F., the autoclave contents were sampled and the solid product was found to be 100% ZSM-5 by x-ray diffraction. After a total reaction time of 28.7 hours at 320° F., the autoclave contents were cooled. The resulting solid product was washed by decantation with deionized water and 3500 ppm Primafloc C-7 (Rohm & Haas) until the decant water was Cl⁻ free. The solid product was filtered and dried at 250° F.

500 grams of the dried filter cake product were calcined in $N_2$ for 3 hours at 1000° F.

444 grams of the calcined product were mixed with 2220 cc of 1 N $NH_4NO_3$ solution for 1 hour at ambient temperature. The mixture was vacuum filtered. The ion exchange procedure was repeated. The filter cake was washed with 1776 cc of water and the solid product was dried at 250° F. The sodium content of the final product was less than 0.01%.

The resulting catalyst had a crystal size of 1-2 microns, a para-xylene sorption capacity of 6.5 weight percent and an ortho-xylene sorption time for 30 percent of said capacity of 92 minutes. Both of the latter measurements were made at 120° C. For the para-xylene sorption the hydrocarbon partial pressure was 5.1 mm of mercury. For ortho xylene sorption time the hydrocarbon partial pressure was 3.8 mm of mercury.

EXAMPLE 2

The catalyst of Example 1 was treated with toluene for 5 hours at 1184° F. at a weight hourly space velocity of 50 and one atmosphere pressure. After this treatment, the catalyst, found to contain approximately 4 weight percent of coke, was contacted with toluene at 1022° F., a pressure of 600 psig, a weight hourly space velocity of 40 and a hydrogen to hydrocarbon mole ratio of 10. The liquid product contained 80.7 weight percent toluene (19.3 percent conversion) and 9.6 weight percent xylenes in addition to benzene. The xylene fraction contained 82 percent of para-xylene.

EXAMPLE 3

900 grams of the filter cake obtained in accordance with the procedure of Example 1 after drying at 250° F. were mixed with 588 grams of alumina and 723 grams of water and mulled for 15 minutes. The mixture was extruded through a 1/16 inch die plate. The resulting extrudates were dried at 250° F. for 16 hours. They were then calcined at 1000° F. for 3 hours in flowing $N_2$ (3 volumes $N_2$/volume catalyst/minute). These extrudates were ammonium exchanged in a column with 1 M $NH_4NO_3$ (5 cc of solution per gram of catalyst) for 1 hour. They were washed with water for one minute. The ammonium exchange was then repeated followed by a 15 minute wash with water at 0.5 cc water per gram of catalyst per minute. The material was dried at 250° F. and then calcined 10 hours at 1000° F. in air.

EXAMPLE 4

1.4 grams of the catalyst of Example 3 was selectively precoked by contact with toluene at 1000° F., 400 psig, WHSV (toluene) = 6.5, $H_2$/HC = 0.5 and $N_2$/HC = 3.5 for a period of 168 hours. Conditions were then changed to toluene disproportionation operating conditions of 900° F., $H_2$/HC = 4.0, WHSV = 9.8 and 400 psig. A liquid sample was collected and found to consist of 80.0 weight percent toluene (20% conversion), 8.3% benzene, and 11.4% mixed xylenes. The xylenes contained 81% para isomer. At the end of the run the catalyst contained 16 grams of coke per 100 grams of coke-free catalyst. The coked catalyst sorbed 5.1 grams of para-xylene per 100 grams of zeolite at 120° C. and a para-xylene pressure of 5.1 mm of mercury. At 120° C. and a ortho-xylene pressure of 3.8 mm of mercury, the time for sorption of 30% of xylene capacity is greater than 900 minutes.

EXAMPLE 5

One gram of the catalyst of Example 3 was selectively precoked by contact with toluene at 1050° F., 400 psig, WHSV = 13, $H_2$/HC = 0.5 and $N_2$/HC = 3.5 for a period of 79 hours. Conditions were then changed to toluene disproportionation conditions of 900° F., $H_2$/HC = 4.1, 400 psig and WHSV = 6.5. A liquid sample was collected and found to consist of 73.2 weight percent toluene (26.8% toluene conversion), 11.0% benzene and 15.1% mixed xylenes. The xylenes contained 66% para isomer. At the end of the run the catalyst contained 22 grams of coke per 100 grams of cokefree catalyst.

EXAMPLE 6

One gram of the catalyst of Example 3 was selectively precoked by contact with toluene at 1100° F., 400 psig, WHSV = 20, $H_2$/HC = 0.5, and $N_2$/HC = 3.5 for a period of 37 hours. Conditions were then changed to toluene disproportionation conditions of 900° F., $H_2$/HC = 4, 400 psig and WHSV = 6.5. A liquid sample was collected and found to consist of 77.6 weight percent toluene (22.4% toluene conversion), 8.5% benzene and 13.2% mixed xylenes. The xylenes contained 77% para-isomer. At the end of the run the catalyst contained 23 grams of coke per 100 grams of coke-free catalyst.

EXAMPLE 7

One gram of the catalyst of Example 3 was selectively precoked by contact with toluene at 1050° F., 400 psig, WHSV = 13, $H_2$/HC = 0.25, and $N_2$/HC = 3.75 for a period of 38 hours. Conditions were then changed to toluene disproportionation conditions of 900° F., $H_2$/HC = 4, 400 psig, and WHSV = 6.5. A liquid sample was collected and found to consist of 79.8 weight percent toluene (20.2% toluene conversion), 8.9% benzene, and 11.1% mixed xylenes. The xylenes contained 79% para isomer. At the end of the run the catalyst contained 26 grams of coke per 100 grams of coke-free catalyst.

EXAMPLE 8

One gram of the catalyst of Example 3 was selectively precoked by contact with toluene at 1050° F., 110 psig, WHSV = 13, and $H_2$/HC = 0.50, for a period of 66 hours. Conditions were then changed to toluene disproporationation conditions of 900° F., $H_2$/HC = 4, 400 psig and WHSV = 6.5. A liquid sample was collected and found to consist of 75.7 weight percent toluene (24.3% toluene conversion), 10.1% benzene and 13.5% mixed xylenes. The xylenes contained 71% para-isomer. At the end of the run the catalyst contained 21 grams of coke per 100 grams of coke-free catalyst.

It will be seen from the results of Examples 4, 5 and 6 that the temperature at which precoking is accomplished has a marked effect on the rate at which a given para-xylene selectivity is reached, with the use of higher temperature providing an enhanced para-xylene selectivity after comparable time on stream. These results are more clearly seen by reference to FIG. 1 of the drawing where the relationship between para-xylene selectivity and precoking temperature is shown.

Figure 2:
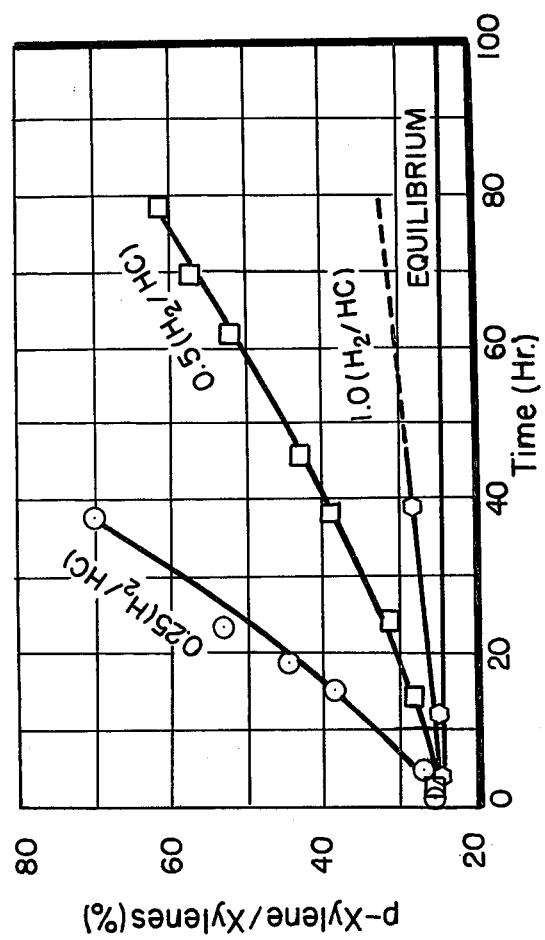
FIG. 2 shows the relationship between the rate of para-xylene selectivity increase and hydrogen to toluene mole ratio during precoking.

Similarly, it will be seen from Examples 5 and 7 that the hydrogen to hydrocarbon ratio maintained during precoking has a substantial effect on the para-xylene selectivity, with the use of lower hydrogen to hydrocarbon (toluene) ratio providing an enhanced para-xylene selectivity after comparable time on stream. These results are more clearly seen by reference to FIG. 2 of the drawing where the relationship between the rate of para-xylene selectivity increase and hydrogen to hydrocarbon mole ratio during precoking is shown.

It is to be understood that the foregoing description is merely illustrative of preferred embodiments of the invention of which many variations may be made by those skilled in the art within the scope of the following claims without departing from the spirit thereof.

We claim:

1. A process for the selective production of paraxylene by disproportionation of toluene in the presence of a catalyst comprising a crystalline aluminosilicate zeolite having a silica to alumina ratio of at least about 12 and a constraint index within the approximate range of 1 to 12, which catalyst has undergone controlled precoking by exposing the same to a thermally decomposable organic compound at a temperature in excess of the decomposition temperature of said compound but less than about 1200° F., at a hydrogen to organic compound mole ratio of between 0 and 1 to deposit at least about 2 weight percent coke thereon and thereafter contacting toluene with the resulting coke-containing catalyst under disproportionation conditions including a temperature between about 800° F. and 1025° F. at a hydrogen to toluene mole ratio greater than 1 and up to about 10 and recovering a product mixture containing para-xylene in an amount greater than the thermodynamic equilibrium concentration thereof in the total xylenes produced.

2. The process of claim 1 wherein said organic compound is a hydrocarbon.

3. The process of claim 1 wherein said organic compound is toluene.

4. The process of claim 1 wherein said disproportionation conditions include a temperature between about 825° F. and 1000° F.

5. The process of claim 1 wherein said precoking is effected at a temperature greater than 1000° F.

6. The process of claim 1 wherein said crystalline aluminosilicate has a crystal size greater than about 0.5 micron.

7. The process of claim 1 wherein said coke-containing catalyst is characterized by a xylene sorption capacity greater than 1 gram/100 grams of zeolite and an ortho xylene sorption time for 30 percent of said capacity of greater than 100 minutes, said sorption capacity and sorption time being measured at 120° C. and a xylene pressure of 4.5±0.8 mm. of mercury.

8. The process of claim 1 wherein said crystalline aluminosilicate is ZSM-5.

9. The process of claim 1 wherein the crystal size of said crystalline aluminosilicate zeolite is within the approximate range of 1 to 20 microns.

10. The process of claim 1 wherein the crystal size of said crystalline aluminosilicate zeolite is within the approximate range of 1 to 6 microns.

11. The process of claim 8 wherein the ZSM-5 is predominately in the hydrogen form.

12. The process of claim 1 wherein said crystalline aluminosilicate zeolite is present in combination with a binder therefor.

13. The process of claim 12 wherein said binder is alumina.

14. The process of claim 12 wherein said crystalline aluminosilicate zeolite is ZSM-5.

15. The process of claim 14 wherein said binder is alumina.

16. The process of claim 1 wherein said disproportionation conditions include a hydrogen to toluene mole ratio between about 1.2 and about 10.

17. The process of claim 1 wherein the amount of coke is between about 2 and about 60 weight percent.

18. The process of claim 1 wherein said precoking is effected at a temperature greater than 1000° F. but less than about 1100° F. at a hydrogen to organic compound mole ratio of between 0.2 and 1.

19. The process of claim 3 wherein said crystalline aluminosilicate zeolite is ZSM-5 of a crystal size greater than about 0.5 micron.

* * * * *